United States Patent [19]

Yamada et al.

[11] Patent Number: 5,352,602
[45] Date of Patent: Oct. 4, 1994

[54] ISOAMYLASE AND PROCESS FOR PRODUCING THE SAME

[75] Inventors: Yuzo Yamada; Toshihiro Sato, both of Shizuoka; Takaichi Ohya, Aichi, all of Japan

[73] Assignee: Amano Pharmaceutical Co., Ltd., Aichi, Japan

[21] Appl. No.: 24,072

[22] Filed: Mar. 1, 1993

[30] Foreign Application Priority Data

Feb. 28, 1992 [JP] Japan .................. 4-078975

[51] Int. Cl.$^5$ .................. C12N 9/44; C12P 19/16
[52] U.S. Cl. .................. 435/210; 435/98; 435/910
[58] Field of Search .................. 435/210, 98, 910

[56] References Cited

U.S. PATENT DOCUMENTS

| | | | |
|---|---|---|---|
| 3,560,345 | 2/1971 | Yokobayashi et al. | 435/210 |
| 3,716,455 | 2/1973 | Ueda et al. | 435/210 |
| 3,723,253 | 3/1973 | Yokobayashi et al. | 435/210 |
| 3,729,380 | 4/1973 | Sugimoto et al. | 435/210 |
| 3,766,014 | 10/1973 | Masuda et al. | 435/210 |
| 4,902,622 | 2/1990 | Nakai et al. | 435/210 |
| 5,147,795 | 9/1992 | Ara et al. | 435/210 |

FOREIGN PATENT DOCUMENTS 1377064 12/1974 United Kingdom .................. 435/210

OTHER PUBLICATIONS

Ueda et al "Applied Microbiol" May 1967 pp. 49–496 vol. 5 No 3.
"World J. Microbiol Biotechnol" (1992) 8, 2, 102–5 Odibo et al.
*Nogei Kagaku Kaishi*, vol. 23, pp. 115–120, pp. 120–123 (1949).
*Bull. Agr. Chem. Soc.*, vol. 19, No. 3, pp. 163–166 (1955).
*FEBS Lett.*, vol. 12, pp. 96–100 (1970).
*Biochem. Biophys. Acta*, vol. 212, pp. 458–469 (1970).

*Primary Examiner*—Herbert J. Lilling
*Attorney, Agent, or Firm*—Sughrue, Mion, Zinn, Macpeak & Seas

[57] ABSTRACT

An isoamylase, useful in the field of starch saccharification, having a molecular weight of about 105,000, an isoelectric point of 6.4, an optimum pH of 3.0 to 5.0, an optimum temperature of about 50° C. and exhibiting temperature stability at 45° C.×10 minutes and pH stability at pH 3.5 to 6.0, and a process for producing the same comprising cultivating an isoamylase-producing strain belonging to the genus Xanthomonas and recovering the enzyme produced.

7 Claims, 4 Drawing Sheets

ISOAMYLASE AND PROCESS FOR PRODUCING THE SAME

FIELD OF THE INVENTION

This invention relates to a substantially pure isoamylase and a process for producing the same. The isoamylase of the present invention specifically cleaves the α-1,6 bonds in glycogen and starches such as amylopectin but does not act on pullulan and can be utilized in the field of starch saccharification, for example, glucose production, fructose production and maltose production.

BACKGROUND OF THE INVENTION

Known microorganisms capable of producing isoamylases include yeast (see *NOGEI KAGAKU KAISHI* Vol. 23, pp. 115-120, pp. 120-123 (1949)), Cytophaga (see *FEBS Lett.*, Vol. 12, pp. 96-100 (1970)), and Pseudomonas (see *Biochem. Biophys. Acta*, Vol. 212, pp. 458-469 (1970)).

These conventional isoamylases have several disadvantages in industrial use. Isoamylase of yeast origin has poor heat stability. Isoamylase of Cytophaga origin has insufficient heat stability and acid resistance. On the other hand, isoamylase of Pseudomonas origin, while such does not have the problem of heat stability and acid resistance, involves disadvantages in productivity, i.e., need of a long cultivation time and low activity attained. Thus, conventional isoamylases are unsatisfactory for use on an industrial scale.

SUMMARY OF THE INVENTION

An object of the present invention is to provide an isoamylase with heat stability and acid resistance.

Another object of the present invention is to provide a process for producing an isoamylase which is heat stable and acid resistant at high productivity.

As a result of extensive research, the inventors have found that a new microorganism strain belonging to the genus Xanthomonas is capable of producing an isoamylase which satisfies the object of the present invention in large quantities. Enzymological examination revealed that the recovered isoamylase is a novel isoamylase. The present invention has been completed based on these findings.

DETAILED DESCRIPTION OF THE INVENTION

Figure 1:
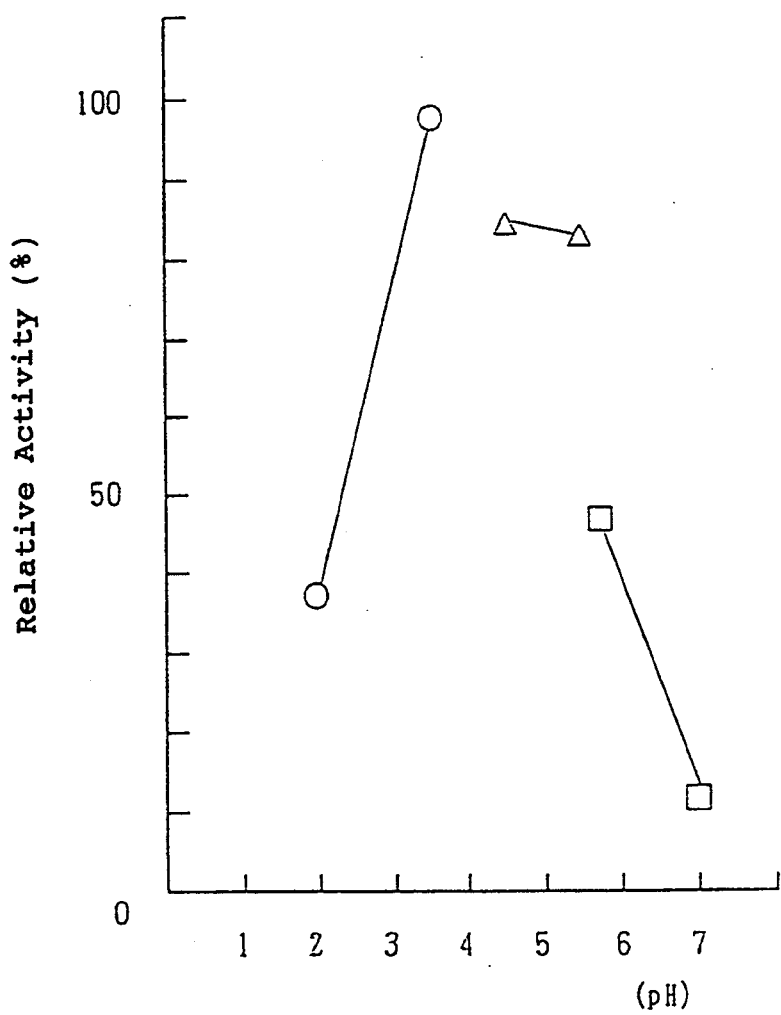
FIG. 1 is a graph showing the relationship between The optimum pH and relative activity (%) of the enzyme according to the present invention. ○ indicates a system using a sodium acetate-HCl buffer solution; Δ an acetate buffer solution; and □ a phosphate buffer solution.

The newly discovered strain which can be used in the present invention was isolated from nature. The microbiological characteristics of the strain are as follows.

A. Morphology
  1) Shape: straight rod
  2) Size: 0.6 to 0.8×1.6 to 5.0 μm
  3) Motility: motile by polar multitrichous flagella. a few motile cells. motile only at a low temperature and in the initial stage of culturing.
  4) Spores: negative B. Growth Characteristics on the Following Media
  1) Meat extract-agar plate culture: small, circular, glossy, and pale yellow colonies (diameter: less than 1 mm); slightly viscous
  2) Litmus milk: peptonization (25 days)

C. Physiological Characteristics:
  1) Nitrate reduction: positive
  2) MR reaction: negative
  3) VP reaction: negative
  4) Indole production: negative
  5) Hydrogen sulfide production: negative
  6) Starch hydrolysis: negative
  7) Utilization of citric acid: negative
  8) Urease: negative
  9) Oxidase: negative
  10) Catalase: positive
  11) Growable Range: Temp.: 7° to 35 °C. (optimum: 25° to 33 °C.) pH: 4.5 to 7.7 (optimum: 5.0 to 5.7)
  12) Behavior to oxygen: strictly aerobic
  13) O-F test: oxidation
  14) Gelatin liquefaction: positive
  15) Production of pigment (King A medium): negative
  16) Casein decomposition: negative
  17) DNA decomposition: positive
  18) Phenylalanine decomposition: negative
  19) Production of acid from sugars:
    1) Fructose: positive
    2) Inositol: positive
    3) Melibiose: positive
    4) Maltose: positive
    5) Cellobiose: positive
    6) Lactose: positive
    7) Xylose: positive
    8) L-Arabinose: positive
    9) Sucrose: positive
    10) Trehalose: positive
    11) Ribose: positive
    12) Salicin: negative
    13) Mannitol: negative
    14) Sorbitol: negative D. Other Characteristics:
  1) Tolerance to sodium chloride: 0 to 3%
  2) Decomposition of Tween 80: negative
  3) Gluconic acid decomposition: negative
  4) Esculin decomposition: positive
  5) Acylamidase: negative
  6) Arginine dihydrolase: negative
  7) Lysine decarboxylase: negative
  8) Ornithine decarboxylase: negative
  9) Utilization of malonic acid: negative
  10) Tyrosine decomposition: positive
  11) ONPG test: negative 12) Poly-β-hydroxybutyric acid accumulation: negative
13) Acid production from 10% Lactose: negative
14) Mucoid production: negative
15) Egg yolk reaction: negative
16) Growth in MacConkey agar medium: positive (weak)
17) Growth in SS (Salmonella-Shigella) medium: negative
18) Acid production in Sellers agar medium: negative
19) Acid production in TSI medium: negative
20) Ubiquinone: Q-8

The above microbiological properties were evaluated with reference to *Bergey's Manual of Systematic Bacteriology*, Vol. 1 (1984). The strain was considered to be a member of the family Pseudomonadaceae from the facts that motility is present in the initial stage of low-temperature culture and in a very small part of cells and that the cells have polar flagella. However, from the fact that the strain does not grow at 37° C., has low tolerance to sodium chloride, prefers a slightly acidic region, has no lysine decarboxylase activity, no oxidase activity or no acylamidase activity, and does not accumulate poly-β-hydroxybutyric acid, it was finally identified to be *Xanthomonas maltophilia*. The strain was designated *Xanthomonas maltophilia* S-517 and a culture was deposited with Fermentation Research Institute, Agency of Industrial Science & Technology, MITI, 1-3, Higaski, 1-chome Tsukuba-shi, Ibaraki-Ken, 305, Japan receiving accession number FERM P-12779 (FERM BP-4205 under the Budapest Treaty). The original deposit was made Feb. 19, 1992 and it was transferred to a deposit under the Budapest Treaty on Feb. 24, 1993.

Carbon sources which can be present in the culture medium for production and accumulation of an isoamylase produced by this microorganism include sugars having an α-1,4 bond or an α-1,6 bond, such as starch, soluble starch, dextrin, acid hydrolysis products of starch, enzyme hydrolysis products of starch, maltose, isomaltose, and maltotriose. Nitrogen sources which can be present in the medium include inorganic nitrogen compounds, e.g., ammonium salts and nitrates, and organic nitrogen compounds, e.g., urea, glutamic acid, aspartic acid, polypeptone, corn steep liquor, meat extract, yeast extract, and hydrolysis products of proteins. Natural media containing carbon sources and nitrogen sources at moderate mixing ratios which mainly comprise rice flour or sweet potato flour may also be used. In addition to the carbon sources and nitrogen sources, the medium may contain appropriate inorganic salts as desired.

Cultivation is carried out by inoculating medium adjusted to pH 6 to 8 with the above-described microorganism strain followed by shake culture or aeration-agitation culture at a temperature of from 20° to 35° C. from 1 to 3 days. After cultivation, the microbial cells are removed from the culture medium to obtain a supernatant liquor as a crude enzyme liquid.

The crude enzyme liquid is then subjected to purification treatments, such as ammonium sulfate fractionation and column chromatography on DEAE-Sepharose CL-6B (produced by Pharmacia), CM-Sepharose CL-6B (produced by Pharmacia), Superose 12 (produced by Pharmacia), etc., to obtain a high purity isoamylase preparation showing a single band in SDS-polyacrylamide gel electrophoresis (hereinafter abbreviated as SDS-PAGE). The enzymological and chemical properties of the purified isoamylase are shown below.

1) Substrate specificity: actively acts on glycogen, also acts on amylopectin, hardly acts on pullulan as shown in Table 1 below.

TABLE 1

| Substrate | V (μmol/min/U) | Initial Velocity (%) |
|---|---|---|
| Glycogen | $6.28 \times 10^{-1}$ | 100 |
| Amylopectin | $2.18 \times 10^{-1}$ | 34.7 |
| Pullulan | $8.45 \times 10^{-3}$ | 1.3 |

Figure 2:
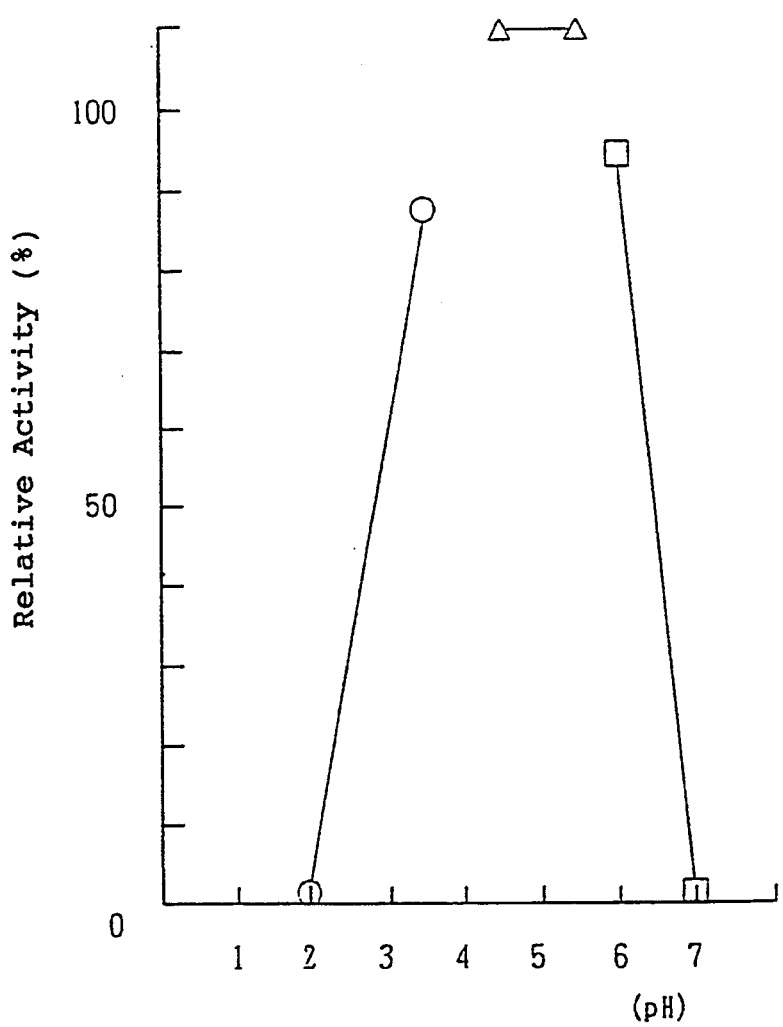
FIG. 2 is a graph showing the relationship between the pH and relative activity (residual activity) (%), i.e., pH stability of the enzyme according to the present invention. The symbols used have the same meanings as in FIG. 1.
Figure 3:
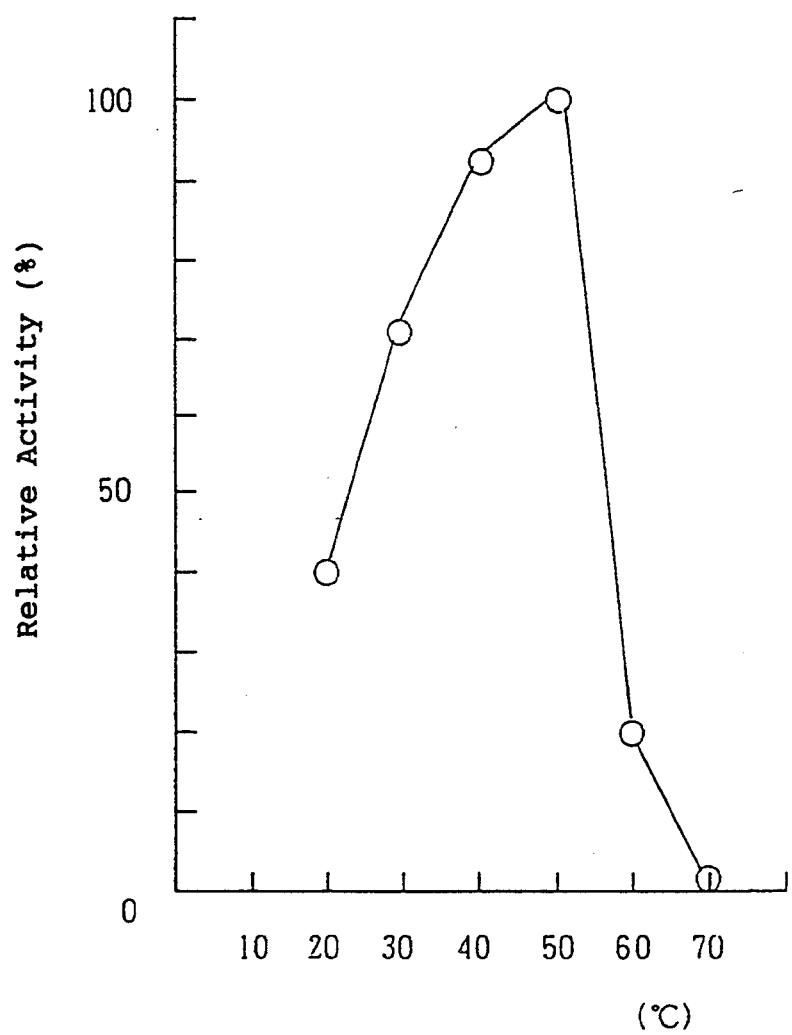
FIG. 3 is a graph showing the relationship between the optimum temperature and relative activity (%) of the enzyme according to the present invention.
Figure 4:
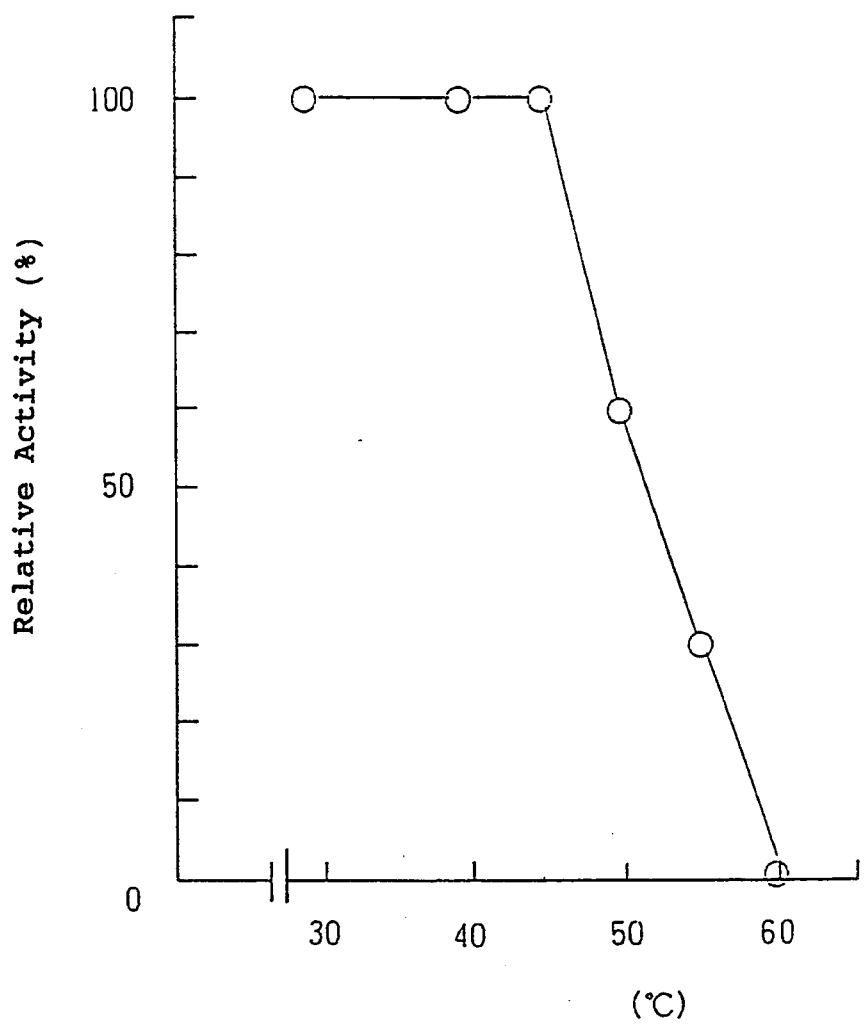
FIG. 4 is a graph showing the relationship between the temperature and relative activity (residual activity) (%), i.e., temperature stability, of the enzyme according to the present invention.

2) Optimum pH: 3.0 to 5.0 (shown in FIG. 1)
3) pH Stability: pH 3.5 to 6.0 (40° C. $\times$ 30 min, shown in FIG. 2)
4) Optimum Temp.: around 50° C. (shown in FIG. 3)
5) Temperature Stability: stable when treated at 45° C. for 10 minutes (shown in FIG. 4)
6) Isoelectric point (pI): 6.4 (Electrofocusing on Ampholine sucrose density gradient)
7) Molecular weight: about 105,000 (measured by gel-filtration on Superose 12; two subunits of 58,000 and 50,000 appear in SDS-PAGE)
8) Influence of inhibitors: Influence of inhibitors and metal salts are shown in Table 2 below.

TABLE 2

| Inhibitor | Concentration (mM) | Percent Inhibition (%) |
|---|---|---|
| N-Bromosuccinimide | 0.01 | 100.0 |
| Potassium iodoiodide | 1 | 4.5 |
| Acetyl monoiodide | 5 | 34.6 |
| Acetyl monoiodide | 0.1 | 10.1 |
| 2,4-Dinitrofluorobenzene | 1 | 2.1 |
| Succinic anhydride | 5 | 8.4 |
| Glucono-1,5-lactone | 10 | 8.0 |
| 2-Hydroxy-5-nitrobenzyl bromide | 0.1 | 14.3 |
| EDTA | 5 | 0 |
| β-Mercaptoethanol | 10 | 31.7 |
| PCMB | 1 | 0 |
| $HgCl_2$ | 1 | 42.2 |
| $CuCl_2$ | 1 | 20.7 |
| $AgNO_3$ | 1 | 98.0 |
| NaF | 1 | 0 |
| $MgCl_2$ | 1 | 26.3 |
| Ammonium molybdate | 1 | 0 |
| NaCl | 1 | 0 |

Enzymological and chemical differences between the novel isoamylase according to the present invention and known isoamylase preparations are tabulated below. Reference is made to the literature cited above. A "hyphen" in Table 3 below indicates that no data was given in the literature.

TABLE 3

| Origin of Isoamylase | Optimum pH | pH Stability | Optimum (°C.) | Temp. Stability (°C.) | pI | Molecular Weight ($\times 10^4$) | Inhibition by Metal Salt (%) |
|---|---|---|---|---|---|---|---|
| Yeast | 6.2 | — | 20 | — | — | 12 | — |
| Cytophaga | 5.5 | — | 40 | 37 | 5.0–5.5 | — | — |
| Pseudomonas | 3–4 | 3–6 | 52 | 45 | 4.4 | 9.4–9.5 | $Mg^{+2}$ (0); |

TABLE 3-continued

| Origin of Isoamylase | Optimum pH | pH Stability | Optimum (°C.) | Temp. Stability (°C.) | pI | Molecular Weight ($\times 10^4$) | Inhibition by Metal Salt (%) |
|---|---|---|---|---|---|---|---|
| Xanthomonas maltophilia S-517 (Invention) | 3–5 | 3.5–6.0 | 50 | 45 | 6.4 | 10.5 | NaF (19); PCMB (34) $Mg^{+2}$ (26.3); NaF (0); PCMB (0) |

In contrast to the enzymological and chemical properties of known isoamylase preparations, it is apparent from the data in Table 3 that the enzyme of the present invention is a novel enzyme. That is, the enzyme of the present invention has different isoelectric point and molecular weight as compared to the enzyme derived from Pseudomonas, and the enzyme of the present invention is not inhibited by NaF and PCMB but inhibited by Mg ions, whereas the enzyme derived from Pseudomonas is not inhibited by Mg ions but inhibited by NaF and PCMB.

Measurements of activity of the enzyme of the present invention were made as follows in accordance with the method of Maruo-Kobayashi (see NIHON NOGEI KAISHI, Vol. 23, pp. 115-120 (1949).

A reaction system consisting of 2.0 ml of a 1.0% soluble starch (glutinous rice) solution, 0.4 ml of a 0.5M acetate buffer solution (pH=3.5), and 0.4 ml of an enzyme liquid was allowed to react at 40° C. for 30 minutes. To the reaction system was added 0.4 ml of a 0.01N iodine solution. After dilution with water to 10 ml, the absorbance at 610 nm was measured. The enzyme activity on an absorbance increase of 0.1 within 1 hour was taken as 10 units.

The enzyme of the present invention can be utilized in the field of saccharification by employing the conventional methods (cf. U.S. Pat. No. 3,795,584, GB-A-2,099,823, etc.).

The present invention is now illustrated in greater detail by reference to the following Examples, but it should be understood that the present invention is not deemed to be limited thereto. Unless otherwise indicated herein, all parts, percents, ratios, and the like are by weight.

EXAMPLE 1

Medium (100 ml) containing 1.5% soluble starch, 0.5% meat extract, 0.3% $(NH_4)_2HPO_4$, 0.1% $K_2HPO_4$, and 0.1% $MgSO_4 \cdot 7H_2O$ (starting pH: 5.5) was inoculated with Xanthomonas maltophilia S-517 (FERM-P 12779), followed by spinner culture in a Sakaguchi flask at 30° C. for 20 hours to produce an isoamylase in culture. The microbial cells were removed by centrifugation, and the resulting supernatant liquor (isoamylase activity: 305 unit/ml) was concentrated using an ultrafilter. Cold ethyl alcohol was added to a concentration of 80% to precipitate the enzyme. The precipitate was collected by centrifugation and lyophilized to obtain isoamylase powder. The recovery of the crude enzyme from the supernatant liquor was 95%.

EXAMPLE 2

In a 30 l jar fermentor was placed 20 l of a medium containing 2.0% maltose, 0.5% sodium glutamate, 0.5% yeast extract, 0.3% $(NH_4)_2HPO_4$, 0.1% $K_2HPO_4$, and 0.1% $MgSO_4 \cdot 7H_2O$ (starting pH: 5.5) and the medium was inoculated with Xanthomonas maltophilia S-517 (FERM-P 12779), followed by aeration culture at 30° C. for 16 hours. The microbial cells were removed by centrifugation, and the resulting supernatant liquor (isoamylase activity: 320 unit/ml) was 20-fold concentrated using an ultrafilter. The concentrate was salted out with 60% saturated ammonium sulfate. The precipitate was dissolved in a phosphate buffer solution (pH=6.0) and passed through DEAE-Sepharose CL-6B. The effluent was then treated with CM-Sepharose CL-6B and eluted with a 0.1M acetate buffer solution (pH=4.5) with a concentration gradient. The combined active fraction was subjected to gel filtration on Superose 12 to obtain $2.76 \times 10^5$ unit/mg-protein of a purified enzyme preparation. The recovery of the purified enzyme from the culture supernatant liquor was 83%.

According to the present invention, a novel isoamylase which is heat stable and acid resistant can be produced in large quantities by culturing Xanthomonas maltophilia in a short time. The present invention thus provides an economical process for producing a useful isoamylase.

While the invention has been described in detail and with reference to specific examples thereof, it will be apparent to one skilled in the art that various changes and modifications can be made therein without departing from the spirit and scope thereof.

What is claimed is:

1. Substantially pure isoamylase produced by cultivating an isoamylase-producing Xanthomonas maltophilia strain, said substantially pure isoamylase having the following enzymological and chemical properties:
   1) Substrate specificity: actively acts on glycogen, also acts on amylopectin, hardly acts on pullulan,
   2) Optimum pH: 3.0 to 5.0,
   3) pH Stability: pH 3.5 to 6.0,
   4) Optimum Temp.: around 50° C.,
   5) Temperature Stability: stable at 45° C. for 10 minutes,
   6) Isoelectric point: 6.4, and
   7) Molecular weight: about 105,000, as measured by gel-filtration on SUPEROSE 12.

2. A process for producing an isoamylase having the following enzymological and chemical properties:
   1) Substrate specificity: actively acts on glycogen, also acts on amylopectin, hardly acts on pullulan,
   2) Optimum pH: 3.0 to 5.0,
   3) pH Stability: pH 3.5 to 6.0,
   4) Optimum Temp.: around 50° C.,
   5) Temperature Stability: stable at 45° C. for 10 minutes,
   6) Isoelectric point: 6.4, and
   7) Molecular weight: about 105,000, as measured by gel-filtration on SUPEROSE 12, comprising cultivating an isoamylase-producing strain belonging to the genus Xanthomonas and recovering the isoamylase produced.

3. The process of claim 2, wherein the isoamylase-producing strain belonging to the genus Xanthomonas is *Xanthomonas maltophilia*.

4. The substantially pure isoamylase of claim 1, wherein the strain of *Xanthomonas maltophilia* is *Xanthomonas maltophilia* S-517.

5. The process of claim 3, wherein the strain of *Xanthomonas maltophilia* is *Xanthomonas maltophilia* S-517.

6. The substantially pure isoamylase of claim 4, wherein the strain of *Xanthomonas maltophilia* S-517 is that having accession number FERM BP-4205.

7. The process of claim 5, wherein the strain of *Xanthomonas maltophilia* S-517 is that having accession number FERM BP-4205.

* * * * *